United States Patent [19]

Popescu et al.

[11] Patent Number: 4,708,861

[45] Date of Patent: Nov. 24, 1987

[54] LIPOSOME-GEL COMPOSITIONS

[75] Inventors: Mircea C. Popescu; Alan L. Weiner, both of Plainsboro; Sharon S. Carpenter-Green, East Windsor, all of N.J.

[73] Assignee: The Liposome Company, Inc., Princeton, N.J.

[21] Appl. No.: 695,887

[22] Filed: Jan. 31, 1985

Related U.S. Application Data

[63] Continuation-in-part of Ser. No. 580,212, Feb. 15, 1984, abandoned.

[51] Int. Cl.$^4$ .................. A61K 43/00; A61K 49/00
[52] U.S. Cl. .................. 424/1.1; 264/4.1; 264/4.32; 428/402.2; 435/1; 424/9; 424/22; 424/31
[58] Field of Search .......... 424/1.1, 9, 22, 31; 428/402.2; 435/1; 264/4.1, 4.32

[56] References Cited

U.S. PATENT DOCUMENTS

| | | | |
|---|---|---|---|
| 3,179,600 | 4/1965 | Brockett | 428/402.2 |
| 3,937,668 | 2/1976 | Zolle | 424/1.1 |
| 4,010,038 | 3/1977 | Iwasaki et al. | 264/4.3 |
| 4,310,505 | 1/1982 | Baldeschwieler et al. | 424/1.1 |
| 4,310,506 | 1/1982 | Baldeschwieler et al. | 424/1.1 |
| 4,377,567 | 3/1983 | Geho | 424/1.1 |
| 4,413,069 | 11/1983 | Marshall | 523/205 |
| 4,431,428 | 2/1984 | Schmer | 604/897 |
| 4,434,153 | 2/1984 | Urquhart et al. | 424/22 |
| 4,439,488 | 3/1984 | Trimnell et al. | 428/402.2 |
| 4,460,560 | 7/1984 | Tökes et al. | 424/1.1 |

*Primary Examiner*—Christine M. Nucker
*Attorney, Agent, or Firm*—Pennie & Edmonds

[57] ABSTRACT

Compositions and methods for maintaining reservoirs of bioactive agents by sequestering the reservoir in a gel matrix are described. In particular, liposomes containing an entrapped bioactive agent are sequestered in a gel matrix. The resulting liposome-gel compositions may be used in vivo or in vitro to provide for sustained release of the bioactive agent. The gel matrix inhibits the dispersion and clearance of the sequestered liposomes without interfering with the ability of the liposomes to release the entrapped bioactive agent. Furthermore, the rate of release of the bioactive agent from the liposome-gel compositions may be varied by altering the composition of the liposomes and/or gels.

78 Claims, No Drawings

LIPOSOME-GEL COMPOSITIONS

CROSS-REFERENCE TO RELATED APPLICATION

This application is a continuation-in-part of application Ser. No. 580,212 filed on Feb. 15, 1984, now abandoned.

TABLE OF CONTENTS

1. Field of the Invention
2. Background of the Invention
   2.1. Liposomes
   2.2. Polymer Matrices and Gels
3. Summary of the Invention
4. Detailed Description of the Invention
   4.1. Preparation of Liposomes
   4.2. Gel Matrices
   4.3. Bioactive Agents
   4.4. Release of Bioactive Agent
   4.5. Use of the Liposome-gel Preparation in Living Systems
5. Example: Liposomes in Methylcellulose
   5.1. Preparation of SPLVs and Methylcellulose Gel
   5.2. Subcutaneous Administration of the SPLV-Methylcellulose Preparation
   5.3. Intramuscular Administration of the SPLV-Methylcellulose Preparation
6. Example: Liposomes in Agarose
   6.1. Preparation of SPLVs and Agarose Gel
   6.2. Intraperitoneal Administration of the SPLV Agarose Preparation
   6.3. Intramuscular Administration of the SPLV-Agarose Preparation
7. Example: Liposomes in Collagen
   7.1. Preparation of SPLVs and Collagen Gel
   7.2. Intramuscular Administration of the SPLV-Collagen Preparation
   7.3. Release of SPLV-entrapped Agent from the Site of Inoculation
   7.4. Subcutaneous Administration and Release of SPLV-entrapped Agent from the Site of Inoculation

1. FIELD OF THE INVENTION

The invention describes compositions and methods for maintaining and immobilizing a reservoir of a biologically active agent which provides for the sustained release of the biologically active agent in living systems.

According to the present invention, a biologically active agent is entrapped in liposomes which are sequestered in a gel matrix. When used in living systems the liposomes sequestered in the gel matrix provide for prolonged release of liposome entrapped agents and the gel matrix provides for immobilization of the liposomes.

According to one embodiment of the present invention, the liposome-gel compositions of the present invention can be implanted in vivo to provide for the prolonged release of the entrapped bioactive agent to the host organism. When administered in vivo, the gel matrix provides for protection of the liposomes from rapid clearance without interfering with release of the liposome entrapped agent. In another embodiment of the present invention, the liposome-gel composition may be used as a support or overlay for cells grown in culture and thus provide for the prolonged release of the entrapped bioactive agent into the culture medium.

2. BACKGROUND OF THE INVENTION

2.1. Liposomes

Liposomes are lipid vesicles which can entrap a variety of pharmaceutical agents and can be used for delivery of these agents to cells and tissues in vivo. A multitude of liposomes can be constructed from one or more lipids such that they are small unilamellar vesicles (SUV), large unilamellar vesicles (LUV), oligolamellar vesicles prepared by reverse phase evaporation (REV), or multilamellar vesicles (MLV). See review by Deamer and Uster, 1983, "Liposome Preparation: Methods and Mechanisms," 1983, in Liposomes, Ostro, ed., Marcel Dekker, Inc., New York, pp. 27–51.

Much has been written regarding the possibilities of using liposomes for drug delivery systems. See for example, the disclosures in U.S. Pat. No. 3,993,754, U.S. Pat. No. 4,145,410. In liposome delivery systems the medicament is entrapped in the liposome which is administered to the patient to be treated. See U.S. Pat. No. 4,224,179 and U.S. Pat. No. 4,235,871.

Aqueous suspensions of liposomes may be inoculated in any desired way (e.g., intravenously, intramuscularly, intraperitoneally, etc.). However, after their inoculation, most of the liposomes are dispersed from the site of inoculation, and either degraded or endocytosed by phagocytic cells such as polymorphonuclear and mononuclear leucocytes, and macrophages (Poste, 1983, Biol. Cell, 47: 19–38). Thus, the release of entrapped drug from liposomes is limited to the period of time between inoculation and degradation or clearance of liposomes from body fluids.

Sustained drug release characteristics can be ascribed to other types of drug microcarriers such as lipid microvesicles (microreservoirs) described by Sears, U.S. Pat. No. 4,298,594.

2.2. Polymer Matrices and Gels

Polymer matrices and gels have been used to localize delivery or retard dispersion of drugs from the site of administration in vivo. Harris et al., 1980, J. Pharm. Sci., 69: 1271–1273, used cross-linked starch gel for localized delivery of prostaglandin E2. Cotes et al., 1980, incorporated human growth hormone into a 16% partially hydrolysed gelatin solution which was subcutaneously injected into animals in an attempt to extend the period of elevated plasma hormone concentration (J. Endocrinol. 87:303–312). More recently, Morimoto et al., 1983, demonstrated enhanced absorption of insulin when the peptide was incorporated into polyacrylic acid aqueous gel bases containing various long chain fatty acids (Internatl. J. Pharm. 14:149–157).

A variety of other polymeric compounds have been utilized to provide sustained-release drug delivery systems, including: silicone elastomers of two types, i.e., the matrix type wherein a powdered drug is dispersed uniformly in a solid phase elastomer, and a membrane type wherein a reservoir of drug is enclosed within a layer of silicone elastomer (Wadsworth and Ratnasooriya, 1981, J. Pharmacol. Methods 6:313–320; see also Cheesman et al., 1982, Fertil. and Sterl. 38:475–481); polymethacrylate or silastic polymers impregnated with progesterone (Ainsworth and Wolynetz, 1982, J. Am. Sci. 54:1120–1127); co-polymers of lactic acid and glycolic acids which provide controlled release of levonorgestrel for six months to one year (Pitt et al., 1981, Natl. Inst. Drug Abuse Res. Monogr. Ser., 28:232–253; Wise et al., 1980, J. Pharm. Pharmacol. 32: 399–403); a fibrin excipient that enables controlled release of biochemical agents (Brown et al. in U.S. Pat. No. 4,393,041); anti-inflammatory and analgesic gel compositions (Noda et al. in U.S Pat. No. 4,393,076; and protective gel compositions for wounds (Mason et al. in U.S. Pat. No. 4,393,048).

3. SUMMARY OF THE INVENTION

This invention describes compositions and methods for maintaining reservoirs of bioactive agents by sequestering the reservoir in a gel matrix. More particularly, liposomes containing bioactive agents are sequestered in a gel matrix which is administered in vivo or in vitro. The gel matrix inhibits both dispersion of the liposomes in vivo or in vitro and clearance of the liposomes in vivo without blocking (1) the diffusion into the gel of body fluids or culture media which interact with the liposome bilayer; (2) the ability of liposomes to release the entrapped agent; or (3) the diffusion of the released agent through the gel to the surrounding environment.

Although incorporation of a bioactive agent directly into a gel matrix may provide for a certain degree of sustained-release, entrapment of a bioactive agent in liposomes can provide for a more prolonged release of the agent because the liposome membrane can be prepared or modified to further retard the leak of the entrapped agent. However, because liposomes themselves are degraded or cleared when administered in vivo, it is difficult to achieve prolonged release of a liposome-entrapped agent in vivo. The present invention is based upon the discovery that sequestering a liposome preparation in a gel matrix, as described herein, protects the liposomes from clearance but does not impair the ability of the liposomes to release their contents slowly.

4. DETAILED DESCRIPTION OF THE INVENTION

According to one embodiment of the present invention, a suspension of liposomes which entrap a biologically active agent is mixed with a suspension of the gel material. The resulting mixture can be administered in vivo to form a gel at the site of administration; alternatively, the preparation can be allowed to gel before administration. Either method of administration results in sequestering the liposomes in the gel matrix at the site of injection; the resistance of the liposomes to clearance or degradation; and the release over a period of time of the liposome-entrapped agent at the site of administration.

In another embodiment of the present invention the liposome-gel preparation may be used in cell or tissue culture systems to provide for the prolonged release of the bioactive agent into the culture medium. The liposome-gel preparation may serve as a support for cell adhesion and growth; alternatively the liposome-gel preparation may be applied to the cell culture as an overlay.

The rate of release of the entrapped bioactive agent is dependent on the type of liposomes used and the composition of the liposome membranes. In fact populations of different liposomes may be sequestered in the gel matrix.

Any type of bioactive agent that can be entrapped in a liposome may be used according to the present invention. Examples of these are listed infra. In fact, two or more bioactive agents entrapped in the same or different populations of liposomes may be sequestered in a gel matrix for use according to the method of the present invention. Finally, one bioactive agent may be entrapped in the liposomes, and the same or a different bioactive agent may be contained in the gel matrix. When this liposome-gel preparation is administered, the bioactive agent contained in the gel matrix is released quickly whereas the bioactive agent entrapped in the sequestered liposomes is released slowly. Thus, when one bioactive agent is entrapped in both the sequestered liposomes and in the gel matrix one dose may provide for both the initial dose of the agent and for its sustained release, thereby avoiding the necessity of administering maintenance doses. Alternatively, when one bioactive agent is entrapped in the sequestered liposomes and another bioactive agent is entrapped within the gel matrix, concurrent therapy using any mixture of bioactive agents is possible. The subsections below are illustrative of the types of liposomes, gels and bioactive agents which may be used in the practice of the present invention.

4.1. Preparation of Liposomes

Liposomes used in the present invention can be prepared by a number of methods, including but not limited to: the original methods of Bangham et al. (1965, J. Mol. Biol. 13:238–252) which yield MLVs; SUVs as described by Papahadjopoulos and Miller (1967, Biochem. Biophys. Acta. 135:624–638); REVs as described by Papahadjopoulos in U.S. Pat. No. 4,235,871; and LUVs as described by Szoka and Papahadjopoulos in 1980, Ann. Rev. Biophys. Bioeng, 9:467–508; as well as methods described in U.S. patent application Ser. No. 476,496 by Lenk et al., filed Mar. 24, 1983 which issued as U.S. Pat. No. 4,522,803 yield stable plurilamellar vesicles (hereinafter referred to as SPLVs); and methods described in U.S. patent application Ser. No. 521,176 by Fountain et al. filed Aug. 8, 1983 which yield monophasic vesicles (hereinafter referred to as MPVs). The procedures for the preparation of SPLVs and MPVs are described below.

SPLVs are prepared as follows: an amphipathic lipid or mixture of lipids is dissolved in an organic solvent. Many organic solvents are suitable, but diethyl ether, fluorinated hydrocarbons and mixtures of fluorinated hydrocarbons and ether are preferred. To this solution are added an aqueous phase and the active ingredient to be entrapped. This biphasic mixture is converted to SPLVs by emulsifying the aqueous material within the solvent and evaporating the solvent. Evaporation can be accomplished during or after sonication by any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture.

In practice, a minimum of about 3 volumes of solvent to about 1 volume of aqueous phase may be used. In fact, the ratio of solvent to aqueous phase can vary up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality of cost-effectiveness, but SPLVs can be made with 15 gm of lipid per ml of aqueous phase.

Most amphipathic lipids may be constituents of SPLVs. Suitable hydrophilic groups include but are not limited to: phosphato, carboxylic, sulphato and amino groups. Suitable hydrophobic groups include but are not limited to: saturated and unsaturated aliphatic hydro-carbon groups and aliphatic hydrocarbon groups substituted by at least one aromatic and/or cycloaliphatic group. The preferred amphipathic compounds are phospholipids and closely related chemical structures. Examples of these include but are not limited to: lecithin, phosphatidyl-ethanolamine, lysolecithin, lysophatidylethanolamine, phosphatidylserine, phosphatidylinositol, sphingomyelin, cardiolipin, phosphatidic acid and the cerebrosides. Specific examples of suitable lipids useful in the production of SPLVs are phospholipids which include the natural lecithins (e.g., egg lecithin or soybean lecithin) and synthetic lecithins, such as saturated synthetic lecithins (e.g., dimyristoyl-phosphatidylcholine, or dipalmitoylphosphatidylcholine or distearoyl-phosphatidylcholine) and unsaturated synthetic lecithins (e.g., dioloylphosphatidylcholine or dilinoloyl-phosphatidylcholine). The SPLV bilayers can contain a steroid component such as cholesterol, coprostanol, cholestanol, cholestane and the like. When using compounds with acidic hydrophilic groups (phosphato, sulfato, etc.) the obtained SPLVs will be anionic; with basic groups such as amino, cationic liposomes will be obtained; and with polyethylenoxy or glycol groups neutral liposomes will be obtained. The size of the SPLVs varies widely. The range extends from about 100 nm to about 10,000 nm (10 microns) and usually about 100 nm to about 1,500 nm. The SPLVs are characterized by a few to over 100 lipid bilayers enclosing aqueous compartments.

The following is an example of the proportions that may be used in SPLV synthesis: SPLVs may be formed by adding 50 micromoles of phospholipid to 5 ml of diethyl ether containing 5 micrograms of butylatedhydroxytoluene (BHT) and then adding 0.3 ml of aqueous phase containing the active substance to be encapsulated. The resultant mixture which comprises the material to be entrapped and the entrapping lipid is sonicated while streaming an inert gas over the mixture thus removing most of the solvent.

Another suitable liposome preparation which may be used is lipid vesicles prepared in a monophasic solvent system, hereinafter referred to as monophasic vesicles or MPVs. MPVs are particularly stable and have a high entrapment efficiency. MPVs are prepared by a unique process as follows: a lipid or a mixture of lipids and an aqueous component are added to an organic solvent or a combination of organic solvents in amounts sufficient to form a monophase. The solvent or solvents are evaporated until a film forms. Then an appropriate amount of aqueous component is added, and the film is resuspended and agitated in order to form the MPVs.

The organic solvent or combination of solvents used in the process must be (1) miscible with water and (2) once mixed with water should solubilize the lipids used to make the MPVs.

For example, an organic solvent or mixture of solvents which satifies the following criteria may be used in the process: (1) 5 ml of the organic solvent forms a monophase with 0.2 ml of aqueous component and (2) the lipid or mixture of lipids is soluble in the monophase.

Solvents which may be used include but are not limited to ethanol, acetone, 2-propanol, methanol, tetrahydrofuran, glyme, dioxane, pyridine, diglyme, 1-methyl-2-pyrrolidone, butanol-2, butanol-1, isoamyl alcohol, isopropanol, 2-methoxyethanol, or a combination of chlorform methanol (e.g., in a 1:1 ratio).

The evaporation should be accomplished at suitable temperatures and pressures which maintain the monophase and facilitate the evaporation of the solvents. In fact, the temperatures and pressures chosen are not dependent upon the phase-transition temperature of the lipid used to form the MPVs. The advantage of this latter point is that heat labile products which have desirable properties can be incorporated in MPVs prepared from phospholipids such as distearoylphosphatidylcholine, which can be formed into conventional liposomes only at temperatures above the phase-transition temperature of the phospholipids. The process usually allows more than 30–40% of the available water-soluble material to be entrapped during evaporation and 2–15% of the available water-soluble material to be entrapped during the resuspension; and up to 70–80% of the available lipid-soluble material can be entrapped if the lipid:drug ratio is increased significantly. With MLVs the entrapment of aqueous phase, which only occurs during the rehydration step since no aqueous phase is present during the drying step, usually does not exceed 10%.

Most lipids may be constituents of MPVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures.

Specific examples of suitable lipids useful in the production of MPVs are phospholipids which include but are not limited to the natural lecithins or phosphatidylcholines (e.g., egg lecithin or soybean lecithin) and synthetic lecithins, such as saturated synthetic lecithins (e.g., dimyristoylphosphatidylcholine or dipalmitoylphosphatidylcholine or distearoylphosphatidylcholine) and unsaturated synthetic lecithins (e.g., dioleoylphosphatidylcholine or dilinoleoylphosphatidylcholine). Other phospholipids include but are not limited to phosphatidylethonolamine, lysolecithin, lysophosphatidylethanolamine, phosphatidylserine, phosphatidylinositol, sphingomyelin, cardiolipin, phosphatidic acid, ceramides and the cerebrosides. The MPV bilayers can contain a steroid component such as cholesterol, coprostanol, cholestanol, cholestane and the like. When using compounds with acidic hydrophilic groups (phosphato, sulfato, etc.) the obtained MPVs will be anionic; with basic groups such as amino, cationic liposomes will be obtained.

MPVs may advantageously be used in delivery systems wherein a bioactive agent is entrapped within the MPV ("entrapped" is defined as entrapment within the aqueous compartment or within the membrane bilayer). In order to entrap one or more agents in MPVs, the agent or agents may be added to the monophase prior to evaporation and formation of the film. Alternatively, the agent or agents may be added with the aqueous component used to resuspend the film and form the MPVs. In fact, to obtain a high entrapment efficiency, the agent or agents may be added to both the monophase and to the aqueous component used to resuspend the film. Two or more agents can also be entrapped in one MPV preparation by adding one agent to the monophase and the other to the aqueous component used to resuspend the film.

4.2. Gel Matrices

Any type of gel matrix may be used in the present invention. The only constraints are (1) the gel matrix must be capable of seqestering the liposomes; i.e., the pores of the gel matrix must be of the appropriate size relative to the size of the liposomes in order to sequester the liposomes in the gel; (2) when used in vivo the gel matrix must be compatible with the recipient organism (i.e., the level of toxicity should be kept to a minimum so as not to outweigh the beneficial effects of administering the bioactive agent in the liposome-gel preparation); (3) the gel must be capable of forming a gel or of remaining gelled at the temperatures and conditions of the environment in which it is administered or applied. For example the gel must remain gelled in the body fluids and at the temperatures to which it is exposed in vivo. Similarly, when used in cell or tissue culture the gel must remain gelled in the culture media and at the incubation temperatures used. Those skilled in the art can appreciate that the gel will degrade with the passage of time, especially when applied in vivo; however, once the sustained delivery of bioactive agent has substantially been accomplished, degradation and metabolism of the gel matrix by the host organism is a desirable result.

Any gel can be used in the practice of the present invention. The materials which can be used to form such gels include but are not limited to: carbohydrates such as cellulosics, methylcellulose, starch and modified starch, agarose, gum arabic, ghatti, karay, tragacanth, guar, locust bean gum, tamarind, carageenan, alginate, xanthan, chickle, collagen, polyacrylamide, polysiloxanes (polyanhydrides, e.g., malic anhydride copolymers, polyacrylates, e.g., hydroxyethylpolymethycrylate polymethylmethacrylate, polyethylethacrylate polymethacrylate, ethylenevinylacetate copolymers, ethylenevinylalcohol copolymers, polyorthoesters, ε-caprolactones, amino acid polymers such as gelled albumin, amino acid polymers and copolymers and gelatins, and other organic or inorganic polymers which can be mixed with liposomes in vitro.

After the mixture forms a gel the resulting liposome-gel matrix can be implanted in tissues. In a particularly useful embodiment of the present invention soft gel matrices such as agarose, collagen and the like containing sequestered liposomes may be injected in vivo.

Alternatively, gels such as methylcellulose can be formed in the tissues after inoculation of liposomes in a suspension containing the gel material. After inoculation the suspension forms a gel and the liposomes remain sequestered in the gel matrix rather than dispersed and cleared.

Regardless of the method used for preparing and implanting the gel matrix, the release of a liposome entrapped bioactive agent is prolonged and the relative concentration of the agent at the site of inoculation is increased.

4.3. Bioactive Agents

Virtually any bioactive agent can be entrapped within the liposomes for use according to the present invention. Such agents include but are not limited to antibacterial compounds, antiviral compounds, antifungal compounds, anti-parasitic compounds, tumoricidal compounds, proteins, toxins, enzymes, hormones, neurotransmitters, lipoproteins, glycoproteins, immunoglobulins, immunomodulators, dyes, radiolabels, radioopaque compounds, fluorescent compounds, polysaccharides, cell receptor binding molecules, anti-inflammatories, antiglaucomic agents, mydriatic compounds, anesthetics, nucleic acids, polynucleotides, etc.

In fact, if concurrent therapy is desired, two or more bioactive agents may be entrapped in one liposome population which is sequestered in the gel matrix. Alternatively, two or more liposome populations (of the same or different types of liposomes, e.g. mixtures of SPLVs, MPVs, SUVs, LUVs, REVs, etc.) which each entrap the same or different bioactive agents may be sequestered in the gel matrix.

In yet another embodiment of the present invention the gel can be used as a vehicle for the same or different bioactive agents than those entrapped by liposomes.

In certain therapeutic applications it may be desired to deliver a relatively high dose of a drug compound (i.e., compound A) followed by a sustained dose of the same or another compound (i.e., compound B). According to the present invention, this is readily accomplished by entrapping compound B in liposomes, sequestering the liposomes in a gel matrix containing compound A, and administering the same in vivo in a single inoculation. Thus, rapid delivery of compound A by diffusion from the gel, and slow sustained delivery of compound B by release from the liposomes is effected

4.4. Release of Bioactive Agent

The release of the bioactive agents may be controlled by the type of liposomes used and the membrane composition of the liposome bilayers as well as by the type and porosity of the gels used. The rate of release is also dependent upon the size and composition of the bioactive agent itself.

The liposome itself is the first rate limiting factor in the release of entrapped bioactive agents. The rate of release may depend upon the number of bilayers, the size of the liposomes and most importantly the bilayer composition.

A number of researchers add "stabilizers" such as sterols, cholesterols and the like to the phospholipid bilayers in order to alter the permeability of the liposome (Papahadjopoulos, D., Kimilberg, H. K., 1974, in Progress in Surface Science, ed. S. G. Davison, pp. 141-232, Oxford: Pergamon; Demel, R. A., Bruckdorf, K. R., Van Deenan, L. L., 1972, Biochem. Biophys. Acta, 255:331-347). For the present invention it is important that the stable liposomes will release their contents upon contact with body fluids or culture media. For a particularly useful liposome preparation, see U.S. patent application Ser. No. 516,268, by Fountain, filed July 22, 1983, which describes liposome preparations containing a titratable agent incorporated into the membrane which allows for a controlled release of the liposome entrapped agent. Thus the rate of release may be controlled by modifying liposome membranes accordingly.

The gel matrix may be the second rate limiting factor in the release of the bioactive agent. In general, for low molecular weight bioactive agents (e.g., approximately 2,000 Daltons or less in molecular weight) the porosity of the gel matrix will not be relevant to the rate of release of bioactive agent because in most cases these agents of low molecular weight will freely diffuse through any gel. For example, most antibiotic compounds will freely diffuse through gel matrices of the present invention. In this situation the composition of the liposome membrane will be more important in determining the rate of release of entrapped agent.

On the other hand, pore size of the gel may become a rate limiting factor in diffusion of the bioactive agent which is released from the sequestered liposomes when the bioactive agent is of a greater molecular weight. Generally, polyacrylamide gels exclude molecules of $10^6$ Daltons or larger in molecular weight. The pore size of a polyacrylamide gel depends upon the concentration of acrylamide used to make the gel (generally 4 to 20% acrylamide is used to prepare these gels). The pore size can be varied further by the extent of crosslinking of the gel. If the molecular weight of the liposome-entrapped bioactive agent is known, one skilled in the art could prepare a gel to obtain the approximate diffusion rate desired by controlling the acrylamide concentration and crosslinking of the gel.

Soft gels such as methylcellulose, collagen and agarose can be used to control the diffusion of larger molecules that are excluded by polyacrylamide gel (e.g., molecules greater than or equal to $10^6$ Daltons in molecular weight) and thus may be used to control the release of bioactive agents of still larger molecular weight. As previously explained, the upper limit on pore size of the gel must be determined with a view to sequestering the liposomes. It should be noted that the use of the soft gels is not limited to the release of agents of larger moleculer weight. Soft gels could also be made to control the diffusion of smaller molecules as well. The porosity of soft gels is also controlled by its concentration as well as other factors.

In addition to the parameters such as size of the bioactive agent and porosity of the gel which may be used to control the rate of diffusion of bioactive agents released from the sequestered liposomes, the nature of the bioactive agent itself and the gel will further affect the rate of diffusion. Thus, if the bioactive agent has any affinity for the gel matrix (e.g., affinity based upon charge, hydrogen bonding, van der Waals forces, etc.) diffusion through the gel of the bioactive agent released from the sequestered liposomes will be slowed.

Finally, no matter what gel matrix is used to sequester liposomes containing an entrapped bioactive agent, the matrix will be freely permeable to fluids to which it is exposed, e.g., to tissue or body fluids or culture media except the molecules which have molecular weights higher than the permeability limit of the gel. Thus, the liposomes within the gel matrix will interact only with molecules which are able to diffuse through the gel matrix. This is important since the interaction of body fluids or culture media with the liposome membrane may be a significant factor in altering the permeability of the liposome membrane.

4.5. Use of the Liposome-Gel Preparation in Living Systems

The liposome-gel compositions of the present invention may be used for sustained delivery of a bioactive agent to cells and/or fluids in vivo and in vitro. A number of embodiments are discussed below.

When used in vivo, the liposome-gel compositions of the present invention may be administered before or after gel formation. Routes of administration include but are not limited to: inoculation or injection, (e.g., intraperitoneal, intramuscular, subcutaneous, intra-aural, intra-articular, intra-mammary, etc.), topical application (e.g., on areas, such as eyes, ears, skin or on afflictions such as wounds, burns, etc.), and by absorption through epithelial or mucocutaneous linings (e.g. vaginal and other epithelial linings, gastrointestinal mucosa, etc.).

For example the liposome-gel preparations of the present invention may be inoculated in vivo to provide for the sustained systemic release of the bioactive agent. Such applications may be particularly useful for the systemic release of drugs such as hormones (e.g., to control growth, fertility, sugar metabolism, etc.) or antimicrobials to control and treat infections, etc.

In an alternative example, the liposome-gel preparation may be applied topically. Topical application may be particularly useful for the treatment of wounds (either surgical or non-surgical wounds) where the sustained release of antimicrobials and/or blood clotting factors may be helpful in the healing process. Similarly, the liposome-gel preparation may be topically applied to burns for the sustained release of antimicrobials and/or cell growth factors. The liposome-gel preparation may also be applied in the ear to treat infections by providing sustained release of antimicrobials; this would reduce the necessity of repeated applications of the bioactive agent in the form of ear drops.

In another alternative embodiment, the liposome-gel preparation may be administered orally for sustained release. Such application may be useful for sustained release to oral epithelium and other oral tissues and for sustained release to epithelia of the alimentary tract.

The liposome-gel preparations of the present invention may also be used in vitro to provide for sustained release of a bioactive agent into the cell or tissue culture medium. Such bioactive agents may include but are not limited to nutrients, drugs, hormones, growth factors, etc. The liposome-gel preparation may be used as a support for cell adhesion and growth; for instance, a liposome-collagen gel may be especially useful for culturing muscle cells, nerve cell, or liver cells. When the liposome-gel preparation is applied as an overlay, a liposome-agarose gel may be particularly useful.

The specific embodiments described above and below are given by way of example only and the invention is limited only by the appended claims.

5. EXAMPLE: LIPOSOMES IN METHYLCELLULOSE

5.1. Preparation of SPLVs and Methylcellulose Gel

SPLVs containing radiolabeled gentamicin sulfate ($^{125}$I-GS/SPLVs) were prepared as described in Section 4.1: 100 mg egg phosphatidylcholine (egg PC) was added to 5 ml diethylether to which 0.3 ml phosphate buffered saline (PBS) containing $^{125}$I-p-hydroxyphenyl propionic acid derivatized gentamicin sulfate ($^{125}$I-GS) was added. The SPLVs were formed by sonicating the resultant mixture while evaporating the diethylether under a stream of nitrogen. The SPLVs were resuspended in 1 ml PBS.

A 2% solution of methylcellulose usually 400-2000 centipoise in PBS pH 7.2 was prepared by mixing at 4° C. until homogeneous, autoclaving at 120° C. and cooling for 24 hours at 4° C.

5.2. Subcutaneous Administration of the SPLV-Methylcellulose Preparation

An aliquot of the 2% methylcellulose solution was mixed with an equal aliquot of the $^{125}$I-GS/SPLV suspension at room temperature. Aliquots (0.1 ml) of this mixture (the $^{125}$I-GS/SPLV-methylcellulose preparation) were inoculated subcutaneously in the abdominal region of adult Swiss Webster mice. Two groups of control mice were treated as follows: one group was inoculated subcutaneously in the abdominal region with 0.1 ml 1% methylcellulose (prepared as described in section 5.1) containing $^{125}$I-GS (i.e., the $^{125}$I-GS was not entrapped in SPLVs); the second group was inoculated subcutaneously in the abdominal region with 0.1 ml of the $^{125}$I-GS/SPLVs suspended in PBS (as prepared in section 5.1). Since methylcellulose forms a gel at 37° C., shortly after subcutaneous inoculation of the methylcellulose preparations (within seconds) a semi-solid "bump" formed under the skin. This bump was visible or palpable for at least 24 hours. In contrast, the inocula of SPLVs suspended in PBS which were inoculated subcutaneously in the control group of mice did not result in the formation of any visible or palpable sign that lasted more than a few minutes.

The subcutaneous immobilization of $^{125}$I-GS was verified by measuring the levels of $^{125}$I-GS in the area of inoculation. To this end, skin and underlying tissues around the site of inoculation (approx. 1.5 cm$^2$ of abdominal ventral wall) were excised 24 hours after inoculation and radioactivity was determined using a gamma counter. The results (Table I) indicated that indeed liposomes were immobilized at the site of inoculation by the methylcellulose gel matrix.

TABLE 1

RETENTION OF RADIOLABELED GENTAMICIN SULFATE AT THE SITE OF SUBCUTANEOUS INOCULATION IN MICE

| Inoculum | % Radiolabel Remaining after 24 hours |
|---|---|
| $^{125}$I-GS/SPLV-methylcellulose | 83.7 |
| $^{125}$I-GS/SPLVs in PBS | 15.0 |
| $^{125}$I-GS in methylcellulose | 3.5 |

5.3. Intramuscular Administration of the SPLV-Methylcellulose Preparation

In another similar experiment, mice were inoculated intramuscularly in the lower femoral region of the leg with 0.05 ml of the $^{125}$I-GS/SPLVs-methylcellulose preparation. The control mice were inoculated with an equivalent amount of the $^{125}$I-GS/SPLVs suspended in PBS. At intervals post inoculation the mice were sacrificed, the entire leg dissected and the radioactivity in the limb determined. The results shown in Table 2 demonstrate that the radioactivity decreased more rapidly in the legs of control mice than in the legs of mice which received the liposome-gel inoculation.

TABLE 2

RETENTION OF RADIOLABELED GENTAMICIN SULFATE AT THE SITE OF INTRAMUSCULAR INOCULATION IN MICE

| Inoculum | % Radiolabel Remaining after 88 hours |
|---|---|
| $^{125}$I-GS/SPLV-methylcellulose | 96.0 |
| $^{125}$I-GS/SPLV | 46.8 |

Thus, the clearance of $^{125}$I-GS is attenuated when liposomes containing this agent are sequestered in the methylcellulose gel matrix and administered intramuscularly.

6. EXAMPLE: LIPOSOMES IN AGAROSE

6.1. Preparation of SPLVS and Agarose Gel

SPLVs were prepared as described in Section 5.1 using 100 mg egg PC and 0.3 ml PBS containing $^{125}$I-GS or 0.3 ml HEPES buffer containing $^{125}$I-human growth hormone ($^{125}$I-HGH, New England Nuclear).

Solutions of 0.5%-2% agarose (Bio-rad standard low Mr) in water or buffer were prepared by melting the polymer powder at 100° C., then sterilizing the solution at 20° C. by autoclaving. After cooling, the resulting gel was melted at 60° C. The temperature was then decreased to 42° C.

In order to sequester the liposomes and to inoculate the resulting gel-liposome preparation, the following procedure was used:

One volume of agarose solution was mixed with one volume of SPLVs suspended in PBS buffer (pH 7.2). This suspension was immediately aspirated into a needle having a large internal diameter (1.5 mm) using a syringe adapted to the needle. The syringe was placed horizontally at 4° C. to permit the agarose to gel. The gel containing liposomes is a cylinder (its volume depending on the internal diameter of the needle and the amount of aspirated solution) which can be easily extruded and inoculated.

6.2. Intraperitoneal Administration of the SPLV Agarose Preparation

Adult Swiss-Webster mice were inoculated intraperitoneally with $^{125}$I-GS/SPLVs sequestered in 1% agarose gel (one gel cylinder/mouse). After 24 hr, the mice were sacrificed, the gels were recovered and their radioactivity determined. The results showed that 95% of the initial radioactivity was associated with the recovered gels indicating that the liposomes were efficiently sequestered and maintained at the site of inoculation.

6.3. Intramuscular Administration of the SPLV Agarose Preparation $^{125}$I-HGH/ SPLVs were sequestered in 0.5-2% agarose gels. Adult Swiss-Webster mice were inoculated intramuscularly in the leg with 0.1 ml of the $^{125}$I-GS/SPLV-agarose gel preparation. Groups of control mice were inoculated intramuscularly in the leg with 0.1 ml of $^{125}$I-GS/SPLVs suspended in HEPES buffer, pH 7.2; agarose gels containing $^{125}$I-HGH (i.e., the $^{125}$I-HGH was not entrapped in SPLVs); or $^{125}$I-HGH in HEPES buffer. At intervals post-inoculation, the mice were sacrificed, the inoculated leg dissected and the residual radioactivity determined. The results are presented in Table 3.

The results in Table 3 indicate that the in vivo retention of $^{125}$I-HGH is prolonged when the hormone is entrapped in the SPLVs or when the hormone is sequestered in the agarose gel; however, the hormone is optimally retained at the site of inoculation when the liposomes containing the hormone are sequestered in a gel matrix.

TABLE 3

RETENTION OF GROWTH HORMONE AT THE INTRAMUSCULAR SITE OF INOCULATION

| | % of $^{125}$I-Growth Hormone Remaining in Leg | | | | | | |
|---|---|---|---|---|---|---|---|
| | Hours | | Days | | | | |
| Inoculum[1] | 3-5 | 24 | 2 | 3 | 7 | 14 | 28 |
| $^{125}$I-HGH | 5.0 | 0.7 | ND | 0.2 | 0.3 | 0.1 | ND |
| $^{125}$I-HGH/ | 81.0 | 57.0 | ND | 16.0 | 0.7 | 0.4 | ND |

TABLE 3-continued
RETENTION OF GROWTH HORMONE AT THE INTRAMUSCULAR SITE OF INOCULATION

| | % of $^{125}$I-Growth Hormone Remaining in Leg | | | | | | |
|---|---|---|---|---|---|---|---|
| | Hours | | Days | | | | |
| Inoculum[1] | 3-5 | 24 | 2 | 3 | 7 | 14 | 28 |
| SPLVs $^{125}$I-HGH/ Agarose | | | | | | | |
| 0.5% | 26.0 | 20.0 | 14.0 | 16.0 | 14.0 | 14.0 | 8.0 |
| 1.0% | 36.0 | 38.0 | 30.0 | 29.0 | 26.0 | 19.0 | 9.0 |
| $^{125}$I-HGH/ SPLV Agarose | | | | | | | |
| 0.5% | 59.0 | 55.0 | 47.0 | 45.0 | 26.0 | 23.0 | 29.0 |
| 1.0% | 74.0 | 63.0 | 54.0 | 37.0 | 24.0 | 20.0 | 17.0 |
| 2.0% | 100.0 | 100.0 | ND | 100.0 | 53.0 | 38.0 | ND |

[1]Percentages indicate the final concentration of agarose in the liposome-gel preparation.

7. EXAMPLE: LIPSOMES IN COLLAGEN

7.1. Preparation of SPLVs and Collagen Gel $^{125}$I-HGH/SPLVs were prepared as described in Section 5.1 using 100 mg egg PC and 0.3 ml HEPES buffer containing $^{125}$I-HGH.

A gel of acid soluble rat tail collagen was prepared by a modification of the method described by Michalopoulous and Pitot, 1975, Exper. Cell Res. 94:70–78. Briefly, 1–3 g of rat tail collagen fibers, dissected from 2 rat tails, was suspended in 300 ml of dilute solution of glacial acetic acid in water (1:1000), and stirred at 4° C. for 48 hours. After allowing the mixture to settle for 24 hours, the clear solution of solubilized rat tail collagen was decanted from sedimented collagen fibers. Stock concentrations of acid-solubilized collagen of 0.3% or 0.9% (weight of fibers used per volume of acid solution) were stored cold until use.

The liposomes were sequestered in the gel as follows: 1.7 ml of acetic acid solubilized rat tail collagen (0.3–1%) was mixed with 0.4 ml of a 2 to 1 mixture of 10×concentrated HEPES buffer (50 mM HEPES, 0.75M NaCl, 0.75M KCl) and 0.28M NaOH. Immediately after addition of buffer, an aliquot of $^{125}$I-HGH/SPLVs (0.1 ml to 0.2 ml) suspended in HEPES buffer was added to the solution which was mixed to ensure uniform distribution. This suspension was allowed to gel at 37° C. for 1 hour.

An experiment was done to determine the relationship between the amount of lipids (as liposomes) in gels and the sequestration ability of the gel. Accordingly a 0.2 ml aliquot of various liposome dilutions was added to the rat tail collagen in HEPES buffer as described above and allowed to gel at 37° C. for 1 hour. Liposomes which were not sequestered in the gel were removed by filtration under vacuum through a nylon mesh filter (81.2 μ pore size; McMaster-Carr Supply Co., Dayton, NJ). Radioactivity in the gel collected on the filter was determined. Table 4 illustrates that approximately 54–74% of the $^{125}$I-HGH/SPLVs could be sequestered in a 0.3% collagen gel.

Table 4 also demonstrates that the quantity of liposomes which could be sequestered in the collagen gel might be increased by increasing the concentration of collagen in the gel to 0.9%.

Another liposome preparation (Table 4) contained fibronectin covalently crosslinked to lipids. The glycoprotein fibronectin which has high affinity for collagen was covalently cross-linked to the liposome bilayer by an enzyme catalyzed method described in U.S. patent application Ser. No. 533,583 by Weiner et al., filed Sept. 19, 1983. Briefly, $^{125}$I-HGH/SPLVs were prepared as described Section 5.1 using egg PC and phosphatidylethanolamine (8:2 mole %) and Tris (tris (hydroxymethyl)aminomethane) saline buffer containing $^{125}$I-HGH. In order to covalently link the fibronectin to the liposomes the $^{125}$I-HGH/SPLV suspension was incubated for 2 hours at 37° C. with 1 mg fibronectin (Seragen Inc., Boston, MA; or Collaborative Research Inc., Lexington, MA) in 1 ml Tris saline buffer with 20 mM CaCl$_2$, 100 μg Factor XIII (trans-glutaminase, Alpha Therapeutic Corp., Los Angeles, CA); 1 unit thrombin (Sigma, St. Louis, MO). (One unit of thrombin will clot a 25 mg % fibronectin solutions in 15 seconds at 37° C.). After incubation the fibronectin modified-SPLVs ($^{125}$I-HGH/FN-SPLVs) were pelleted at 10,000×g for 10 minutes, and washed 3 times.

TABLE 4
SEQUESTRATION OF LIPOSOMES IN A COLLAGEN GEL MATRIX

| Lipid Added to Gel | % Collagen | % Radiolabel Sequestered Within Gel |
|---|---|---|
| $^{125}$I-HGH/SPLVs (0.2 ml) | | |
| 100.0 mg | 0.3 | 54 |
| 33.3 mg | 0.3 | 57 |
| 12.3 mg | 0.3 | 74 |
| 7.9 mg | 0.3 | 72 |
| 5.0 mg | 0.3 | 66 |
| 3.8 mg | 0.3 | 71 |
| 10.0 mg | 0.9 | 81 |
| $^{125}$I-HGH/FN-SPLVs (0.2 ml) | | |
| 8.3 mg | 0.3 | 86 |

As illustrated in Table 4, when fibronectin-modified liposomes were added to the collagen gel, a significantly enhanced sequestration of liposomes was achieved.

7.2. Intramuscular Administration of the SPLV-Collagen Preparation

In order to determine the effect of liposome sequestration on the retention of growth hormone in tissues, adult Swiss Webster mice were inoculated intramuscularly in the leg with the $^{125}$I-HGH/SPLV or $^{125}$I-HGH/FN-SPLV sequestered in 0.3% collagen gels (prepared as described above in Section 7.1). Control groups were inoculated with $^{125}$I-HGH/SPLVs suspended in buffer, or $^{125}$I-HGH in buffer. At intervals post-inoculation, mice were sacrificed, the inoculated legs dissected and the residual radioactivity determined.

The results (Table 5) show that the hormone is optimally retained at the site of inoculation when the liposomes containing the hormone are sequestered in the collagen gel matrix. Modification of the liposome membrane by the attachment of fibronectin, despite a greater sequestration of liposomes in collagen gel (see Table 4) did not significantly enhance retention of bioactive agent at the site of inoculation. However a more linear rate of release of $^{125}$I-growth hormone in this group was observed.

TABLE 5
RETENTION OF GROWTH HORMONE AT THE INTRAMUSCULAR SITE OF INOCULATION

| Inoculum | % of $^{125}$I Human Growth Hormone Remaining in leg[a] | | | | |
|---|---|---|---|---|---|
| | Hours | | Days | | |
| | 3-5 | 24 | 3 | 7 | 14 |
| $^{125}$I-HGH | 5.0 | 1.0 | 0.2 | 0.3 | 0.1 |
| $^{125}$I-HGH/SPLVs | 81.0 | 57.0 | 16.0 | 1.0 | 0.4 |
| $^{125}$I-HGH/SPLVs-Collagen | 78.0 | 57.0 | 55.0 | 27.0 | 19.0 |
| $^{125}$I-HGH/FN-SPLVs-Collagen | 82.0 | 77.0 | 54.0 | 40.0 | 7.0 |

[a]Mean values of three mice/group.

In another experiment, sustained release of $^{125}$I-HGH from liposomes sequestered in collagen gel prepared using Vitrogen, a commercially available pepsin and acid digested bovine dermal collagen, was compared with that observed when the gel was prepared using the acid-solubilized rat collagen.

Vitrogen, a product of the Collagen Corp., was obtained from Flow Laboratories (McLean, VA). A gel of Vitrogen (0.3%) was prepared according to manufacturer's instructions. The liposomes containing entrapped $^{125}$I-HGH were sequestered in the gel as described in Section 7.1.

Adult Swiss Webster mice were inoculated intramuscularly in the leg with $^{125}$I-HGH/SPLV or $^{125}$I-HGH/FN-SPLV sequestered in 0.3% collagen gels prepared using either rat tail acid solubilized collagen or bovine (Vitrogen) collagen. Control groups were inoculated with $^{125}$I-HGH/SPLV suspended in buffer or free $^{125}$I-HGH suspended in rat tail acid solubilized collagen gel. At intervals post-inoculation, mice were sacrificed, the inoculated legs dissected, and the residual radioactivity determined.

As illustrated in Table 6, although sequestration of liposomes in Vitrogen gel enhanced retention of hormone at the site of inoculation at 7 days post-inoculation, this gel was not as effective as the acid solubilized rat tail collagen. Modification of the sequestered liposomes with fibronectin significantly enhanced retention of hormone at the site of inoculation with both forms of the gel at 1 day post-inoculation, but not at 7 days post-inoculation for the Vitrogen gel.

TABLE 6
RETENTION OF GROWTH HORMONE AFTER INTRAMUSCULAR INOCULATION: EFFECT OF VARIOUS LIPOSOME COLLAGEN MATRICES

| Inoculum | % of $^{125}$I Human Growth Hormone Remaining in leg[a] | |
|---|---|---|
| | Days | |
| | 1 | 7 |
| $^{125}$I-HGH/Rat Tail Collagen | 1.0 | 0.2 |
| $^{125}$I-HGH/SPLVs | 57.0 | 1.0 |
| $^{125}$I-HGH/SPLVs-Rat Tail Collagen | 57.0 | 27.0 |
| $^{125}$I-HGH/FN-SPLVs-Rat Tail Collagen | 77.0 | 40.0 |
| $^{125}$I-HGH/SPLVs Vitrogen | 42.6 | 14.3 |
| $^{125}$I-HGH/FN-SPLVs-Vitrogen | 75.8 | 15.4 |

[a]Mean values of five mice/group.

7.3. Release of SPLV Entrapped Agent from Site of Inoculation

An additional experiment was done to verify whether the growth hormone released in vivo from the liposomes sequestered in a collagen gel is in an active (functional) form. Bovine growth hormone (BGH) was entrapped in SPLVs (BGH-SPLV) prepared essentially as described in Section 5.1 at a ratio of 1.75 mg BGN/100 mg egg PC. A 0.25 ml aliquot of the BGH-SPLVs (containing 1.75 mg BGH) were sequestered in a 0.8% collagen gel (as described in section 7.1) which was then inoculated intramuscularly in female 39 days old Sprague Dawley rats which were hypophysectomized at 25 days of age (Charles River Inc.). Control animals were not treated after hypophysectomy. The growth of the rats was determined daily and expressed in grams by subtracting the body weight at the time of inoculation from the actual weight post inoculation. The results (Table 7) show that the group of animals treated with the BGH/SPLV-collagen gel preparation gained weight steadily, indicating that the growth hormone was released from the collagen-sequestered liposomes and retained its activity. No gain in weight was observed in the control group of rats.

TABLE 7

WEIGHT GAIN IN HYPOPHYSECTOMIZED RATS

| Treatment | Change in grams[a] Days | | | | | | | |
|---|---|---|---|---|---|---|---|---|
| | 1 | 2 | 3 | 4 | 5 | 6 | 7 | 8 |
| Untreated | 0 | 0 | −0.8 | −0.8 | −0.2 | 0.5 | −0.4 | −0.9 |
| BGH/SPLV-Collagen Single Injection | 1.2 | 3.9 | 4.7 | 7.3 | 8.7 | 9.4 | 9.6 | 9.9 |

[a]Mean values of 8 rats/group.

7.4. Subcutaneous Administration and Release of SPLV-Entrapped Agent From the Site of Inoculation SPLVs containing insulin (insulin/SPLVs) were prepared as described in Section 4.1: 100 mg dipalmitoyl phosphatidylcholine was dissolved in 5 ml diethyl ether. To this was added 0.3 ml of aqueous buffer (either PBS or 0.01M Tris) at pH 7.4. containing 15 mg bovine insulin (25 unit/mg) (Sigma Chemical CO., St. Louis, MO). In order to solubilized the insulin in the aqueous buffer, it was necessary first to partition the hormone powder into a solution (50 mg/ml) of sonicated small unilamellar vesicles composed of EPC. Following solubilization, the aqueous droplet was emulsified into the ether phase by sonicating under a stream of nitrogen until the ether was completely evaporated. The lipid/insulin paste was rehydrated to form insulin/SPLVs. The insulin/SPLVs were washed three times in buffer containing 10 mm $CaCl_2$. The $CaCl_2$ facilitated pelleting of the insulin/SPLVs. Entrapment of insulin as determined by $^{14}$C-insulin label was 20-30%.

Sustained release of insulin from insulin/SPLVs and insulin/SPLVs sequestered in collagen gel was examined in a diabetic animal model.

Diabetes was developed in Sprague-Dawley rats, supplied by either Charles River Laboratories (Wilmington, MA) or Hilltop Laboratory Animals (Scottsdale, PA) by intraperitoneal injection of streptozotocin, 50 mg/kg on two consecutive days. Two weeks post-injection, diabetes was assessed by measuring water consumption, urine volume and urine glucose. Urine glucose was determined using a glucose assay kit No. 15-UV (Sigma Chemical CO., St. Louis, MO).

Insulin/SPLVs were sequestered in collagen gel (0.9% collagen) as described in Section 7.1. Experimental animals received a single subcutaneous injection of insulin/SPLVs in the collagen gel in the hind limb corresponding to 4 mg insulin/kg body weight. Control animals received a single subcutaneous injection of either free insulin in buffer, free insulin in collagen gel, or free insulin/SPLVs in an amount equivalent to experimental animals. A minimum of five animals was used for each group.

As illustrated in Table 8, urine glucose values were depressed in diabetic rats which received a single subcutaneous injection of either free insulin/SPLVs or insulin/SPLVs sequestered in collagen gel. In animals treated with insulin/SPLVs only, however, the maximum glucose depression (hence, greatest insulin release) was seen at 8 hours post-treatment. Glucose in urine began to rise again in these animals after 24 hours. On the other hand, in animals treated with insulin/SPLVs sequestered in collagen gel, maximum glucose depression was seen at 2 days post-treatment. A statistically significant greduction in urine glucose was still evident one week post-treatment. This indicates that sequestration of the liposomes in collagen gel impedes the release of insulin to the systemic circulation because no difference would be expected if the release of insulin was solely a liposome dependent phenomenon.

It should be noted that free insulin subcutaneously injected was rapidly cleared (within 4 hours) from the systemic circulation (data not shown).

TABLE 8

SYSTEMIC RELEASE OF INSULIN AFTER SUBCATANEOUS A ADMINISTRATION
% Change In Urine Glucose From Untreated Diabetic Animals[a]

| Animal[b] | Hours | | Days | | |
|---|---|---|---|---|---|
| | 4 | 8 | 1 | 2 | 7 |
| Normal (non-diabetic)[c] | 5.8 | 10.3 | 10.4 | 5.3 | 24 |
| Untreated Diabetic | 123.9 | 144.5 | 128.4 | 222.0 | — |
| Insulin/SPLVs Diabetic | 63.4 | 27.6 | 52.4 | 104.8 | 69.6 |
| Insulin/SPLVs-Collagen Diabetic | 69.9 | 51.8 | 55.7 | 9.3 | 38.9 |

[a]Represents % change from value of urine glucose output (mg/dl) at time = 0.
[b]Mean values of five rats/group. Rats injected with a single injection of free insulin in buffer cleared the hormone in 4 hours (data not shown).
[c]Normal denotes non-treated non-diabetic animals included for comparison.

What is claimed is:

1. A liposome-gel composition comprising a bioactive agent entrapped in liposomes sequestered in a gel matrix in which:
   (a) the gel matrix has a pore size relative to the liposomes so that the liposomes are sequestered in the gel matrix without blocking (i) diffusion of fluids into the gel which interact with bilayers of the liposomes, (ii) the ability of the sequestered liposomes to release the entrapped bioactive agent or (iii) the diffusion of the bioactive agent released from the liposomes through the gel to the surrounding environment; and
   (b) the gel matrix is capable of forming or remaining gelled at temperatures and conditions of the environment in which it is administered or applied.

2. The lipsosome-gel composition according to claim 1 wherein said gel comprises an inorganic polymer.

3. The liposome-gel composition according to claim 1 wherein said gel comprises an organic polymer.

4. The liposome-gel composition according to claim 1 wherein said gel is in a gelled form.

5. The liposome-gel composition according to claim 1 wherein said gel is in an ungelled form.

6. The liposome-gel composition according to claim 1 wherein said gel comprises a celluosic.

7. The liposome-gel composition according to claim 1 wherein said gel comprises methylcellulose.

8. The liposome-gel composition according to claim 1 wherein said gel comprises agarose.

9. The liposome-gel composition according to claim 1 wherein said gel comprises collagen.

10. The liposome-gel composition according to claim 1 wherein said gel comprises gumarabic, ghatti, karay, tragacanth, guar, locust bean gum, tamarind, carageenan, alginate, xanthan or chickle.

11. The liposome-gel composition according to claim 1 wherein said gel comprises polyacrylamide.

12. The liposome-gel composition according to claim 1 wherein said gel comprises polysiloxane.

13. The liposome-gel composition according to claim 1 wherein said gel comprises polyacrylate.

14. The liposome-gel composition according to claim 13 wherein said polyacrylate comprises hydroxyethylpolymethycrylate.

15. The liposome-gel composition according to claim 1 wherein said gel comprises polymethylmethacrylate.

16. The liposome-gel composition according to claim 1 wherein said gel comprises polyethylethyacrylate.

17. The liposome-gel composition according to claim 1 wherein said gel comprises polymethacrylate.

18. The liposome-gel composition according to claim 1 wherein said gel comprises lactic acid-glycolic acid copolymer.

19. The liposome-gel composition according to claim 1 wherein said gel comprises ε-caprolactone.

20. The liposome-gel composition according to claim 1 wherein said gel comprises ethylenevinylacetate copolymer.

21. The liposome-gel composition according to claim 1 wherein said gel comprises ethylenevinylalcohol copolymer.

22. The liposome-gel composition according to claim 1 wherein said gel comprises a polyanhydride.

23. The liposome-gel composition according to claim 21 wherein said polyanhydride comprises malic anhydride.

24. The lipsome-gel composition according to claim 1 wherein said gel comprises polyorthoester.

25. The liposome-gel composition according to claim 1 wherein said gel comprises an amino acid polymer or copolymer.

26. The liposome-gel composition according to claim 1 wherein said gel comprises gelatin.

27. The liposome-gel composition according to claim 1 wherein said gel comprises starch or modified starch.

28. The liposome-gel composition according to claim 1 wherein said liposomes are multilamellar vesicles.

29. The liposome-gel composition according to claim 1 wherein said liposomes are small unilamellar vesicles.

30. The liposome-gel composition according to claim 1 wherein said liposomes are reverse phase evaporated vesicles.

31. The liposome-gel composition according to claim 1 wherein said liposomes are large unilamellar vesicles.

32. The liposome gel-composition according to claim 1 wherein said liposomes are stable plurilamellar vesicles.

33. The liposome-gel composition according to claim 1 wherein said liposomes are monophasic vesicles.

34. The liposome-gel composition according to claim 1 wherein said liposomes sequestered in the gel comprise a plurality of different types of liposomes.

35. The liposome-gel composition according to claim 1 wherein a plurality of bioactive agents are entrapped in said liposomes.

36. The liposome-gel composition according to claim 34 wherein a plurality of bioactive agents are entrapped in said liposomes.

37. The liposome-gel composition according to claim 1 wherein said bioactive agent entrapped in liposomes is selected from the group consisting of: antibacterial, antifugal, antiviral, and antiparasitic compounds.

38. The liposome-gel composition according to claim 37 wherein said antibacterial compound is gentamicin or a derivative thereof.

39. The liposome-gel composition according to claim 1 wherein said bioactive agent entrapped in liposomes is a cell receptor binding compound.

40. The liposome-gel composition according to claim 1 wherein said bioactive agent entrapped in liposomes is selected from the group consisting of: hormones, neurotransmitters, tumoricidal compounds, growth factors, and toxins.

41. The liposome-gel composition according to claim 40 wherein said bioactive agent is growth hormone.

42. The liposome-gel composition according to claim 41 wherein said growth hormone is human growth hormone.

43. The liposome-gel composition according to claim 40 wherein said bioactive agent is insulin.

44. The liposome-gel composition according to claim 1 wherein said bioactive agent entrapped in liposomes is selected from the group consisting of: proteins, glycoproteins, and lipoproteins.

45. The liposome-gel composition according to claim 44 wherein said glycoprotein is an immunoglobulin.

46. The liposome-gel composition according to claim 1 wherein said bioactive agent entrapped in liposomes is an immunomodulating compound.

47. The liposome-gel composition according to claim 1 wherein said bioactive agent entrapped in liposomes is selected from the group consisting of catalysts and enzymes.

48. The liposome-gel composition according to claim 1 wherein said bioactive agent entrapped in liposomes is selected from the group consisting of: dyes, radiolabels, radioopaque compounds and fluorescent compounds.

49. The liposome-gel composition according to claim 1 wherein said bioactive agent entrapped in liposomes is selected from the group consisting of: anti-inflammatory, antiglaucomic, mydriatic, analgesic and anaesthetic compounds.

50. The liposome-gel composition according to claim 1 wherein said bioactive agent entrapped in liposomes is selected from the group consisting of: nucleic acids and polynucleotides.

51. The liposome-gel composition according to claim 1 wherein said bioactive agent entrapped in liposomes is selected from the group consisting of: monosaccharides, disaccharides, and polysaccharides.

52. The liposome-gel composition according to claim 1 further comprising a bioactive agent sequestered in the gel.

53. The liposome-gel composition according to claim 52 wherein the bioactive agent sequestered in the gel is different from the bioactive agent entrapped in the liposomes.

54. The liposome-gel composition according to claim 52 wherein the bioactive agent sequestered in the gel is the same as the bioactive agent entrapped in the liposomes.

55. The liposome-gel composition according to claim 52 wherein said bioactive agent sequestered in the gel is selected from the group consisting of: antibacterial, antifungal, antiviral, and antiparasitic compounds.

56. The liposome-gel composition according to claim 52 wherein said bioactive agent sequestered in the gel is a cell receptor binding compound.

57. The liposome-gel composition according to claim 52 wherein said bioactive agent sequestered in the gel is selected from the group consisting of: hormones, neurotransmitters, tumoricidal compounds, growth factors and toxins.

58. The liposome-gel composition according to claim 52 wherein said bioactive agent sequestered in the gel is selected from the group consisting of: proteins, glycoproteins, and lipoproteins.

59. The liposome-gel composition according to claim 52 wherein said glycoprotein sequestered in the gel is an immunoglobulin.

60. The liposome-gel composition according to claim 52 wherein said bioactive agent sequestered in the gel is an immunomodulating compound.

61. The liposome-gel composition according to claim 52 wherein said bioactive agent sequestered in the gel is selected from the group consisting of catalysts and enzymes.

62. The liposome-gel composition according to claim 52 wherein said bioactive agent sequestered in the gel is selected from the group consisting of: dyes, radiolabels, radioopaque compounds and fluorescent compounds.

63. The liposome-gel composition according to claim 52 wherein said bioactive agent sequestered in the gel is selected from the group consisting of: anti-inflammatory, antiglaucomic, mydriatic, analgesic and anaesthetic compounds.

64. The liposome-gel composition according to claim 52 wherein said bioactive agent sequestered in the gel is selected from the group consisting of: nucleic acids and polynucleotides.

65. The liposome-gel composition according to claim 52 wherein said bioactive agent sequestered in the gel is selected from the group consisting of: monosaccharides, disaccharides, and polysaccharides.

66. A method for delivery in vivo of a bioactive agent comprising: administering to a host in vivo a liposome composition comprising a bioactive agent entrapped in liposomes sequestered in a gel matrix in which:
  (a) the gel matrix has a pore size relative to the liposomes so that the liposomes are sequestered in the gel matrix without blocking (i) diffusion of fluids into the gel which interact with bilayers of the liposomes, (ii) the ability of the sequestered liposomes to release the entrapped bioactive agent or (iii) the diffusion of the bioactive agent released from the liposomes through the gel to the surrounding environment; and
  (b) the gel matrix is capable of forming or remaining gelled at temperatures and conditions of the environment in which it is administrered or applied
wherein the gel of said composition is compatible with the host and is capable of maintaining its gelled form in the host environment when administered and of degrading over time after administration.

67. A method for delivery in vivo of a bioactive agent comprising: administering to a host in vivo a liposome-gel composition comprising a bioactive agent entrapped in liposomes sequestered in a gel matrix in which:
  (a) the gel matrix has a pore size relative to the liposomes so that the liposomes are sequestered in the gel matrix without blocking (i) diffusion of fluids into the gel which interact with bilayers of the liposomes, (ii) the ability of the sequestered liposomes to release the entrapped bioactive agent or (iii) the diffusion of the bioactive agent released from the liposomes through the gel to the surrounding environment; and
  (b) the gel matrix is capable of forming or remaining gelled at temperatures and conditions of the environment in which it is administered or applied
  wherein the gel of said composition is compatible with the host and is capable of maintaining its gelled form in the host environment when administered and of degrading over time after administration and wherein said liposomes sequestered in the gel comprise a plurality of different types of liposomes.

68. A method for delivery in vivo of a bioactive agent comprising: administering to a host in vivo a liposome-gel composition comprising a bioactive agent entrapped in liposomes sequestered in a gel matrix in which:
  (a) the gel matrix has a pore size relative to the liposomes so that the liposomes are sequestered in the gel matrix without blocking (i) diffusion of fluids into the gel which interact with bilayers of the liposomes, (ii) the ability of the sequestered liposomes to release the entrapped bioactive agent or (iii) the diffusion of the bioactive agent released from the liposomes through the gel to the surrounding environment; and
  (b) the gel matrix is capable of forming or remaining gelled at temperatures and conditions of the environment in which it is administered or applied
  wherein the gel or said composition is compatible with the host and is capable of maintaining its gelled form in the host environment when administered and of degrading over time after administration and wherein said liposome further comprises a bioactive agent sequestered in the gel, and wherein the gel of said composition is compatible with the host and capable of maintaining its gelled from in the host environment when administered and of degrading over time after administration.

69. The method according to claim 66 wherein the liposome-gel composition is administered in its gelled form.

70. The method according to claim 66 wherein the liposome-gel composition attains its gelled form after administration in vivo.

71. The method according to claim 66 wherein said route of administration is intraperitoneal.

72. The method according to claim 66 wherein said route of administration is intramuscular.

73. The method according to claim 66 wherein said route of administration is subcutaneous.

74. The method according to claim 66 wherein said route of administration is intra-articular.

75. The method according to claim 66 wherein said route of administration is intra-aural.

76. The method according to claim 66 wherein said route of administration is ocular.

77. The method according to claim 66 wherein said route of administration is topical.

78. The method according to claim 66 wherein said route of administration is oral.

* * * * *